United States Patent
Du et al.

(10) Patent No.: US 11,753,392 B2
(45) Date of Patent: Sep. 12, 2023

(54) METHOD FOR SYNTHESIS OF DEUTERATED AMIDE AND DEUTERATED SULFONAMIDE

(71) Applicant: HINOVA PHARMACEUTICALS INC., Sichuan (CN)

(72) Inventors: Wu Du, Sichuan (CN); Kun Wen, Sichuan (CN); Jinyun He, Sichuan (CN); Haibo Li, Sichuan (CN); Dekun Qin, Sichuan (CN); Xinghai Li, Sichuan (CN); Yuanwei Chen, Sichuan (CN)

(73) Assignee: HINOVA PHARMACEUTICALS INC., Sichuan (CN)

( * ) Notice: Subject to any disclaimer, the term of this patent is extended or adjusted under 35 U.S.C. 154(b) by 0 days.

(21) Appl. No.: 17/047,380

(22) PCT Filed: Apr. 12, 2019

(86) PCT No.: PCT/CN2019/082555
§ 371 (c)(1),
(2) Date: Oct. 13, 2020

(87) PCT Pub. No.: WO2019/196945
PCT Pub. Date: Oct. 17, 2019

(65) Prior Publication Data
US 2021/0115009 A1 Apr. 22, 2021

(30) Foreign Application Priority Data
Apr. 13, 2018 (CN) .......... 201810332134.1

(51) Int. Cl.
C07D 401/04 (2006.01)
C07C 231/24 (2006.01)
C07D 233/02 (2006.01)
C07D 401/06 (2006.01)

(52) U.S. Cl.
CPC .......... *C07D 401/04* (2013.01); *C07C 231/24* (2013.01); *C07D 233/02* (2013.01); *C07D 401/06* (2013.01); *C07C 2601/14* (2017.05); *C07C 2601/16* (2017.05)

(58) Field of Classification Search
CPC .. C07D 401/04; C07D 233/02; C07D 401/06; C07C 231/24; C07C 2601/14; C07C 2601/16
See application file for complete search history.

(56) References Cited

U.S. PATENT DOCUMENTS

| 9,346,764 B2 * | 5/2016 | Chen ............ A61P 43/00 |
| 2007/0041933 A1 * | 2/2007 | Simanek ........ C07D 401/14 977/754 |
| 2009/0062347 A1 | 3/2009 | Czarnik |
| 2009/0082573 A1 * | 3/2009 | Hagadorn ........ C07D 213/38 546/329 |
| 2016/0130194 A1 * | 5/2016 | Howard, Jr. ...... C07D 251/42 544/212 |

FOREIGN PATENT DOCUMENTS

| CN | 103159680 A | 6/2013 |
| CN | 104211683 A | 12/2014 |

OTHER PUBLICATIONS

Liu et al. Org. Lett. 2017, 19, 1614-1617 and its supporting information (Year: 2017).*
Bhatia et al. Indian Journal of Chemistry 2013, 52B, 379-386 (Year: 2013).*
Shi et al. Chem. Commun., 2017, 53, 10584-10587 (Year: 2017).*
Meng et al. Org. Lett. 2017, 19, 2158-2161 (Year: 2017).*
Liu, Y. M. et al. "Metal-Free Transamidation of Secondary Amides via Selective N—C Cleavage under Mild Conditions" Organic Letters, vol. 19, Mar. 14, 2017, ISSN: 1523-7060, pp. 1614-1617.
Meng, G. R. et al. "A General Method for Two-Step Transamidation of Secondary Amides Using Commercially Available, Air- and Moisture-Stable Palladium/NHC (N-Heterocyclic Carbene) Complexes", Organic Letters, vol. 19, Apr. 11, 2017, ISSN: 1523-7060, pp. 2158-2161.
Shi, S. C. et al. "Pd-PEPPSI:a general Pd—NHC precatalyst for Buchwald-Hartwig cross-coupling of esters and amides (transamidation) under the same reaction conditions" ChemComm, vol. 53, Sep. 12, 2017, ISSN: 1359-7345, pp. 10584-10587.
Dander, J. E. et al. Nickel-catalyzed transamidation of aliphatic amide derivatives Chemical Science, vol. 8, Jul. 10, 2017, ISSN: 2041-6539, pp. 6433-6438.

* cited by examiner

*Primary Examiner* — Matthew P Coughlin
(74) *Attorney, Agent, or Firm* — NKL Law; Allen Xue

(57) ABSTRACT

A novel method for synthesizing deuterated amides and deuterated sulfonamides includes the following steps: (1) adding a compound M, DMAP, $R^3$—X to a solvent to obtain a compound N after a reaction is complete; and (2) adding the compound N, $R^4$—NH—$R^5$, or a salt and base thereof to a solvent, and purifying after a reaction is complete to obtain a compound I.

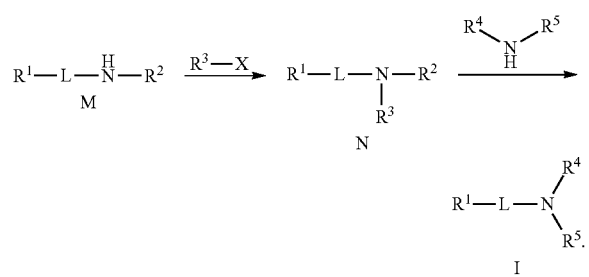

26 Claims, No Drawings

US 11,753,392 B2

METHOD FOR SYNTHESIS OF DEUTERATED AMIDE AND DEUTERATED SULFONAMIDE

TECHNICAL FIELD

The present invention relates to a new method for synthesis of deuterated amide and deuterated sulfonamide.

BACKGROUND ART

Deuterated drugs are currently a hot research field in the development of new drugs. Deuterated drugs denote that part of the hydrogen atoms in drug molecules is/are substituted with deuterium. Since in drug molecules, deuterium is close to hydrogen in shape and volume, deuterated drugs can generally retain the biological activity and selectivity of the original drug. Because C-D bond is more stable than C—H bond, C-D bond is less likely to be broken in the metabolic reaction of deuterated drug, and its half-life may be extended, and the metabolites may be reduced, thereby achieving better pharmacokinetics. Currently, one deuterated drug AUSTEDO (deutetrabenazine) has been approved for marketing, and several deuterated drugs are in the clinical stage. Therefore, it is of great significance to develop new synthetic methods of deuterated compounds.

Enzalutamide is an androgen-receptor (AR) antagonist, and suitable for prostate cancer patients treated with the antineoplastic drug docetaxel. Enzalutamide is the newest method for treatment of this disease, that has been proven to prolong the life of patients. Apalutamide (ARN-509) is a selective and competitive androgen receptor inhibitor, and effective for treatment of prostate cancer. Sorafenib is a novel multi-targeted oral drug for treatment of tumors, and its primary development goal is to treat gastrointestinal stromal tumors and metastatic renal cells that do not respond to or cannot tolerate standard therapies. Sorafenib can selectively target the receptors of certain proteins, which are thought to play a molecular switch-like role during tumor growth. Regorafenib is a multi-target inhibitor that acts on VEGFR1/2/3, PDGFR β, Kit, RET, and Raf-1. Rebastinib is a Bcr-Abl inhibitor. Axitinib can be used for advanced kidney cancer in which other systemic treatments have failed. Sumatriptan is a 5-HT1 receptor agonist.

Above-mentioned drugs are all amides or sulfonamides, and their deuterated compounds have many important uses in drug research. For example, compounds 1, 2, and 3 have entered the clinical or pre-clinical development stage. How to use the above-mentioned drugs to gently and efficiently prepare deuterated drugs is of great significance. They can not only be used as substitute drugs for non-deuterated drugs, but also as isotope standards for drug metabolism studies.

Content of the Invention

In order to solve above problems, the present invention provides a new method for synthesis of deuterated amide and deuterated sulfonamide.

The present invention provides a method for synthesis of deuterated amine, and the steps are as follows:

$$R^1-L-\underset{M}{\overset{H}{N}}-R^2 \xrightarrow{R^3-X} R^1-L-\underset{\underset{R^3}{|}}{N}-R^2 \xrightarrow{\underset{H}{\overset{R^4\diagdown N\diagup R^5}{}}}$$

-continued $$R^1-L-N\diagdown_{R^5}^{R^4}$$
I

In formulas,

L is selected from carbonyl, sulfo;

$R^1$ is selected from the group consisting of substituted or unsubstituted aryl, substituted or unsubstituted heteroaryl, substituted or unsubstituted alkyl, substituted or unsubstituted cycloalkyl, and substituted or unsubstituted heterocyclic group;

$R^2$ is selected from the group consisting of substituted or unsubstituted alkyl, substituted or unsubstituted cycloalkyl, substituted or unsubstituted heterocyclic group, substituted or unsubstituted aryl, and substituted or unsubstituted heteroaryl;

$R^3$ is selected from —CO—$R^6$, —SO$_2$R$^7$; X is a leaving group;

Wherein, $R^6$ and $R^7$ are independently of each other selected from alkoxy, alkyl, substituted alkyl, aryl;

$R^4$ and $R^5$ are independently of each other selected from H, substituted or unsubstituted deuterated alkyl, deuterated cycloalkyl, deuterated heterocyclic group, deuterated aryl, deuterated heteroaryl, as well as $R^4$ and $R^5$ are not hydrogen at the same time;

(1) Compound M, DMAP, and $R^3$—X are added to the solvent, and compound N is obtained after completion of the reaction;

(2) Compound N, $R^4$—NH—$R^5$ or the salt thereof, and the base are added to the solvent, and after completion of the reaction, compound I is obtained by purification.

Further, $R^3$ is selected from —CO—$R^6$, —SO$_2$R$^7$; X is selected from —OR$^3$, Cl, Br;

Wherein, $R^6$ and $R^7$ are independently of each other selected from t-butoxy, isopropoxy, benzyloxy, methyl, trifluoromethyl, phenyl, and tolyl.

Further, $R^3$ is selected from —CO—$R^6$, —SO$_2$R$^7$;

Wherein, $R^6$ is selected from t-butoxy, isopropoxy, benzyloxy; $R^7$ is selected from methyl, trifluoromethyl, phenyl, and tolyl.

Further, $R^3$ is selected from —CO—$R^6$; X is —OR$^3$;

Wherein, $R^6$ is selected from t-butoxy.

Further, $R^4$ and $R^5$ are independently of each other selected from H, deuterated alkyl, as well as $R^4$ and $R^5$ are not hydrogen at the same time.

Further, $R^4$ and $R^5$ are independently of each other selected from H, deuterated methyl, as well as $R^4$ and $R^5$ are not hydrogen at the same time.

Further, $R^2$ is selected from substituted or unsubstituted $C_1$-$C_6$ alkyl.

Further, $R^2$ is selected from substituted or unsubstituted $C_1$-$C_4$ alkyl.

Further, $R^2$ is selected from methyl.

Further, $R^1$ is selected from one of the following structures:

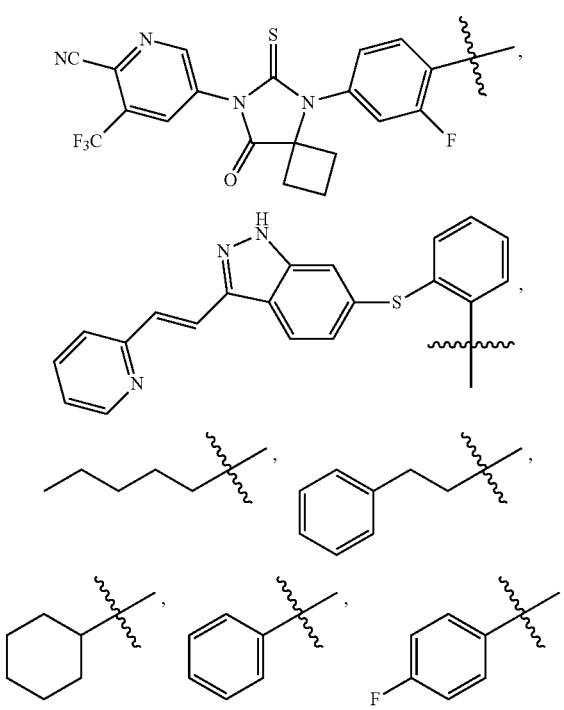

Further, compound I is selected from one of the following structures:

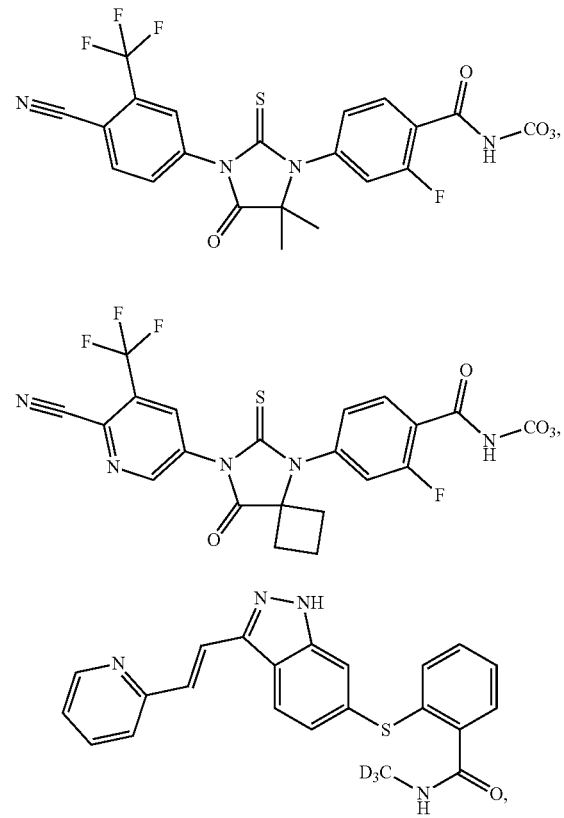

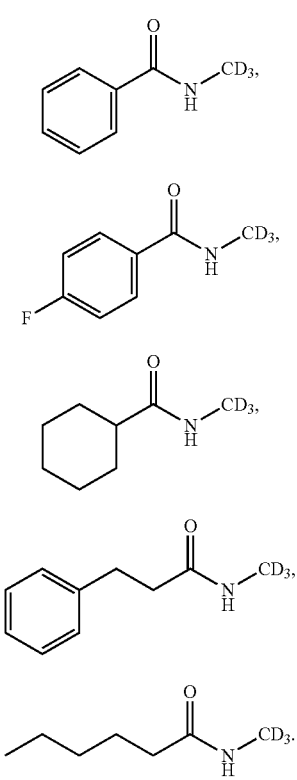

Further, in step (1), said solvents are polar solvents or non-polar solvents.

Further, said polar solvents are selected from the group consisting of dichloromethane, dichloroethane, formamide, trifluoroacetic acid, DMSO, acetonitrile, DMF, hexamethylphosphoramide, methanol, ethanol, acetic acid, isopropanol, pyridine, tetramethylethylenediamine, acetone, triethylamine, n-butanol, dioxane, tetrahydrofuran, methyl formate, tributylamine, methyl ethyl ketone, ethyl acetate, chloroform, trioctylamine, dimethyl carbonate, ethyl ether, isopropyl ether, n-butyl ether, trichloroethylene, and diphenyl ether.

Further, said polar solvent is selected from dichloromethane.

Further, said non-polar solvents are selected from the group consisting of benzene, toluene, carbon tetrachloride, carbon disulfide, cyclohexane, hexane.

Further, in step (1), the molar ratio of compound M, DMAP, and R3-X is 1:1-3:1-10, preferably 1:2-3:1.5-2.

Further, in step (1), the feed ratio of compound M and the solvent is 1:2-20 mmol/mL; preferably 1:2-15 mmol/mL, more preferably 1:5.5-10 mmol/mL.

Further, in step (1), the reaction temperature is 10-60° C.

Further, the reaction temperature is 20-30° C., and preferably 25° C.

Further, in step (1), the reaction time is 10-120 h, preferably 10-16 h, more preferably 10-14 h, and further preferably 12 h.

Further, in step (2), said solvents are polar solvents or non-polar solvents.

Further, said polar solvents are selected from the group consisting of dichloromethane, dichloroethane, formamide, trifluoroacetic acid, DMSO, acetonitrile, DMF, hexamethylphosphoramide, methanol, ethanol, acetic acid, isopropanol, pyridine, tetramethylethylenediamine, acetone, triethylamine, n-butanol, dioxane, tetrahydrofuran, methyl formate, tributylamine, methyl ethyl ketone, ethyl acetate, chloroform, trioctylamine, dimethyl carbonate, ethyl ether, isopropyl ether, n-butyl ether, trichloroethylene, and diphenyl ether.

Further, said polar solvent is selected from acetonitrile.

Further, said non-polar solvents are selected from the group consisting of benzene, toluene, carbon tetrachloride, carbon disulfide, cyclohexane, and hexane.

Further, in step (2), the feeding ratio of compound N and the solvent is 1:1-25 mmol/mL, preferably 1:1-20 mmol/mL, and more preferably 1:2.5-15 mmol/mL.

Further, in step (2), said base is organic base or inorganic base.

Further, said organic base is selected from the group consisting of DBU, sodium methoxide, potassium ethoxide, potassium t-butoxide, sodium t-butoxide, triethylamine, triethylenediamine, DBN, DMAP, pyridine, N-methylmorpholine, tetramethylethylenediamine, TMG, n-butyl lithium, and LDA.

Further, said organic base is selected from DBU.

Further, said inorganic base is selected from the group consisting of potassium hydroxide, barium hydroxide, calcium hydroxide, aluminum hydroxide, lithium hydroxide, magnesium hydroxide, zinc hydroxide, copper hydroxide, iron hydroxide, lead hydroxide, cobalt hydroxide, chromium hydroxide, zirconium hydroxide, nickel hydroxide, ammonium hydroxide, sodium carbonate, sodium bicarbonate, potassium carbonate, and potassium bicarbonate.

Further, in step (2), the molar ratio of compound N, $R^4$—NH—$R^5$ or its salt, and base is 1:1-4:1-5, and preferably 1:1-4:1-4.5.

Further, the molar ratio of compound N, $R^4$—NH—$R^5$ or its salt, and base is 1:3:4.

Further, in step (2), the reaction temperature is 10-100° C., and preferably 20-23° C., and more preferably 25° C.

Further, in step (2), the reaction time is 10-120 h, preferably 10-14 h, and more preferably 12 h.

The compounds and derivatives provided in the present invention can be named according to IUPAC (International Union of Pure and Applied Chemistry) or CAS (Chemical Abstracting Service, Columbus, Ohio) naming system.

For the definition of term used in the present the invention: unless otherwise specified, the initial definition provided for the group or the term herein is applicable to those in the whole specification; for terms not specifically defined herein, according to the disclosure content and the context, the term should have the meaning commonly given by those skilled in the field.

The structure of the compound mentioned in the present invention denotes the one that can exist stably.

"Substitution" means that the hydrogen in a molecule is substituted by other different atoms or molecules.

"Deuterium" denotes the isotope of hydrogen (H), also known as heavy hydrogen, and the elemental symbol is generally D or 2H.

"Alkyls" is a hydrocarbon group formed by losing one hydrogen in an alkane molecule, such as methyl —$CH_3$, ethyl —$CH_3CH_2$, etc.

"Substituted or unsubstituted $C_{1-4}$ alkyls" denotes $C_{1-4}$ alkyls that can be substituted or unsubstituted.

"Aryls" denote all-carbon monocyclic or fused polycyclic (i.e. ring sharing adjacent carbon atom pairs) groups with conjugated π electron system, such as phenyl and naphthyl. Said aryl ring can be fused to other cyclic groups (including saturated and unsaturated rings), but can not contain hetero atoms such as nitrogen, oxygen, or sulfur. At the same time, the point connecting with the parent must be on the carbon in the ring having the conjugated π electron system. Aryls can be substituted or unsubstituted.

"Heteroaryls" denote the heteroaromatic group containing one or more heteroatoms, that contains at least one heteroatom selected from N, O, or S in the ring, and additionally has a fully conjugated π electron system. For example, furanyl, pyrrolyl, quinolinyl, thienyl, pyridyl, pyrazolyl, N-alkylpyrrolyl, pyrimidinyl, pyrazinyl, imidazolyl, tetrazolyl, thienopyridyl, etc. The heteroaromatic ring can be fused to aryls, heterocyclic group or cycloalkyl ring, in which the ring connected with the parent structure is heteroaromatic ring. Heteroaryls can be substituted or unsubstituted.

"Cycloalkyls" denote saturated or unsaturated cyclic hydrocarbon substituents; cyclic hydrocarbon can have one or more rings. For example, "$C_{3-8}$ cycloalkyls" denote cycloalkyls having 3-8 carbons.

"Heterocyclic group" denotes a saturated or unsaturated cyclic hydrocarbon substituent; the cyclic hydrocarbon may be monocyclic or polycyclic, and carry at least one cycloalkyl group containing O, S or substituted nitrogen atom, and other ring atoms are carbons, for example, "$C_{3-8}$ heterocyclic group" denotes a heterocyclic group having a total of 3-8 carbon atoms and heteroatoms. The heterocyclic group may be unsubstituted or substituted by one or more substituents.

Compound 1 is a deuterated drug of anti-prostate cancer Enzalutamide, compound 2 is a deuterated drug of anti-prostate cancer Apalutamide, compound 3 is a deuterated anti-cancer drug Sorafenib, compound 4 is a deuterated anti-cancer drug Regorafenib, compound 5 is Rebastinib, and compound 6 is deuterated Axitinib. Compound 7 is a deuterated drug treating migraine Sumatriptan.

DMAP: 4-dimethylaminopyridine.

Boc$_2$O: Boc anhydride, and the structure is

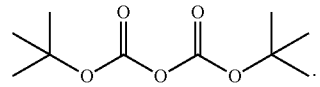

DCM: dichlorinemethane.
DBU: 1,8-diazabicycloundec-7-ene, and the structure is

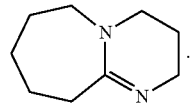

The "room temperature" mentioned in the present invention is "25±5° C.".

"Overnight" mentioned in the present invention is "12±1 h".

The present invention provides a new method for synthesis of deuterated amides and deuterated sulfonamides, in which the reaction conditions are mild, and the route is short, including only two steps. The method can be applied to raw materials unsuitable for using prior art, improve the synthetic efficiency, and used for many amide compounds, with an incredible versatility, thereby providing a new choice for the preparation of deuterated amide and sulfonamide compounds. Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

The starting materials and equipment used in the specific examples of the present invention are all known products and can be obtained by purchasing commercially available products.

Example 1 Synthesis of Compound 1

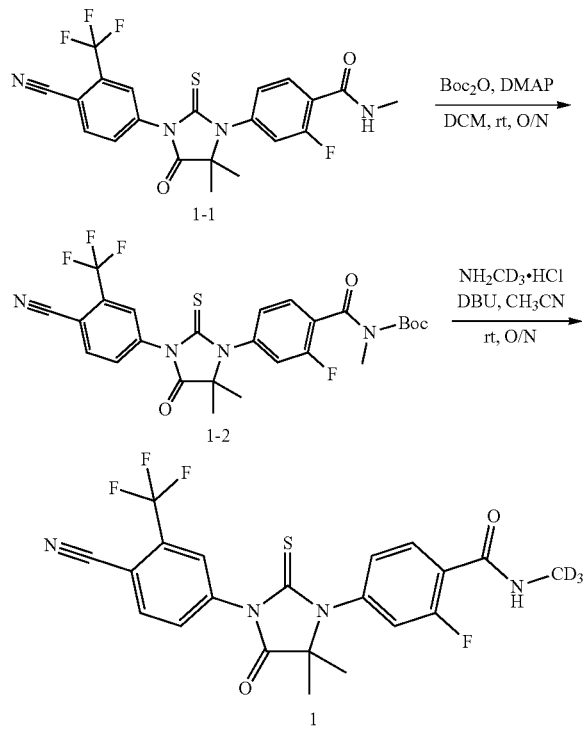

(1) t-Butyl (4-(3-(4-cyano-3-(trifluoromethyl)phenyl)-5,5-dimethyl-4-oxo-2-thioimidazolidin-1-yl)-2-fluorophenyl)(methyl)formamide (1-2)

(4-(3-(4-Cyano-3-(trifluoromethyl)phenyl)-5,5-dimethyl-4-oxo-2-thioimidazolidin-1-yl)-2-fluoro-N-methylbenzamide (1-1, 400 mg, 0.85 mmol) and DMAP (210 mg, 1.7 mmol) were added to 5 mL $CH_2Cl_2$, to which was added Boc anhydride (280 mg, 1.3 mmol). The reactions were stirred at room temperature overnight. After addition of DCM and 0.1 mol/L dilute HCl (50 mL:50 mL), the mixtures were extracted, and the organic layer was washed with saturated brine twice, dried, rotatory evaporated, and purified by silica gel column to obtain white solid t-butyl (4-(3-(4-cyano-3-(trifluoromethyl)phenyl)-5,5-dimethyl-4-oxo-2-thioimidazolidin-1-yl)-2-fluorophenyl)(methyl)formamide (1-2, 450 mg, 0.80 mmol), with a yield of 92.3%.

MS (ESI) m/z 465.1 $(M-100+1)^+$.

(2) (4-(3-(4-Cyano-3-(trifluoromethyl)phenyl)-5,5-dimethyl-4-oxo-2-thioimidazolidin-1-yl)-2-fluoro-N-(deuterated methyl)benzamide (1)

t-Butyl (4-(3-(4-cyano-3-(trifluoromethyl)phenyl)-5,5-dimethyl-4-oxo-2-thioimidazolidin-1-yl)-2-fluorophenyl)(methyl)formamide (1-2, 50 mg, 0.09 mmol) and deuterated methylamine hydrochloride (19 mg, 0.27 mmol) were added to 0.25 mL acetonitrile. White insoluble materials appeared, and DBU (54 mg, 0.36 mmol) was also added, then the solid was dissolved. The resultant mixture was stirred overnight at room temperature, and the sample spot was absorbed on the plate. After developed, the result indicated that the raw material dots disappeared. After addition of DCM and 0.1 mol/L dilute HCl (30 mL:30 mL), the mixtures were extracted, and the organic layer was washed with saturated brine twice, dried, rotatory evaporated, and purified by Pre-TLC to obtain white solid (4-(3-(4-cyano-3-(trifluoromethyl)phenyl)-5,5-dimethyl-4-oxo-2-thioimidazolidin-1-yl)-2-fluoro-N-(deuterated methyl)benzamide (1, 38 mg, 0.09 mmol), with a yield of 92.8%.

MS (ESI) m/z 468.1 $(M+H)^+$.

$^1$H NMR (400 MHz, DMSO-$d_6$) δ 8.52-8.38 (m, 2H), 8.31 (d, J=1.5 Hz, 1H), 8.10 (dd, J=8.3, 1.7 Hz, 1H), 7.80 (t, J=8.1 Hz, 1H), 7.45 (dd, J=10.7, 1.7 Hz, 1H), 7.35 (dd, J=8.2, 1.8 Hz, 1H), 1.55 (s, 6H).

Example 2 Synthesis of Compound 2

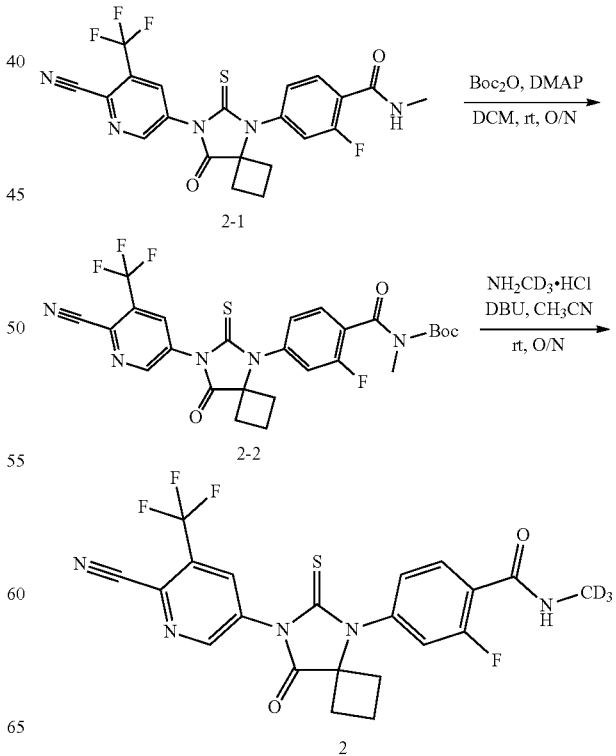

(1) 4-(7-(6-cyano-5-(trifluoromethyl)pyridin-3-yl)-8-oxo-6-thiol-5,7-diazaspiro[3.4]octan-5-yl)-2-fluoro-N-Boc-methylbenzamide (2-2)

4-(7-(6-Cyano-5-(trifluoromethyl)pyridin-3-yl)-8-oxo-6-thiol-5,7-diazaspiro[3.4]octan-5-yl)-2-fluor o-N-methylbenzamide (2-1, 500.0 mg, 1.05 mmol) and DMAP (384.0 mg, 3.15 mmol) were added to 10 mL $CH_2Cl_2$, to which was drop added Boc anhydride (458.0 mg, 1.05 mmol). The reactions were stirred overnight at room temperature. After addition of DCM and 0.1 N dilute HCl (50 mL: 50 mL), the mixtures were extracted, and the organic layer was washed with saturated brine twice, dried, rotatory evaporated, and purified by silica gel column to obtain white solid 4-(7-(6-cyano-5-(trifluoromethyl)pyridin-3-yl)-8-oxo-6-thiol-5,7-diazaspiro[3.4]octan-5-yl)-2-fluoro-N-Boc-methylbenzamide (2-2, 450.0 mg, 0.80 mmol), with a yield of 82.6%.

MS (ESI) m/z 478.0 (M-100+1)$^+$.

(2) 4-(7-(6-Cyano-5-(trifluoromethyl)pyridin-3-yl)-8-oxo-6-thiol-5,7-diazaspiro[3.4]octan-5-yl)-2-fluoro-N-(deuterated methyl)benzamide (2)

4-(7-(6-Cyano-5-(trifluoromethyl)pyridin-3-yl)-8-oxo-6-thiol-5,7-diazaspiro[3.4]octan-5-yl)-2-fluor o-N-Boc-methylbenzamide (2-2, 200.0 mg, 0.35 mmol) was dissolved in 5 mL acetonitrile, to which was added deuterated methylamine hydrochloride (75.0 mg, 1.06 mmol). Insoluble solid appeared, and DBU (215.6 mg, 1.42 mmol) was added, then the solution became clear. The resultant mixture reacted overnight at room temperature. After addition of $CH_2Cl_2$ and 0.1 N dilute HCl (30 mL:30 mL), the mixture was extracted, and the organic layer was washed with saturated brine twice, dried, rotatory evaporated, and purified by Pre-TLC to obtain white solid 4-(7-(6-cyano-5-(trifluoromethyl)pyridin-3-yl)-8-oxo-6-thiol-5,7-diazaspiro[3.4]octan-5-yl)-2-fluor o-N-(deuterated methyl)benzamide (2, 130.0 mg, 0.27 mmol), with a yield of 76.2%.

MS (ESI) m/z 481.0 (M+H)$^+$.

$^1$H NMR (400 MHz, CDCl$_3$) δ 9.09 (d, J=2.1 Hz, 1H), 8.43-8.27 (m, 2H), 7.28 (d, J=1.9 Hz, 1H), 7.17 (dd, J=11.5, 1.8 Hz, 1H), 6.71 (d, J=11.6 Hz, 1H), 2.77-2.69 (m, 3H), 2.57 (dt, J=12.7, 10.2 Hz, 2H), 2.32-2.22 (m, 1H).

Example 3 Synthesis of Compound 3

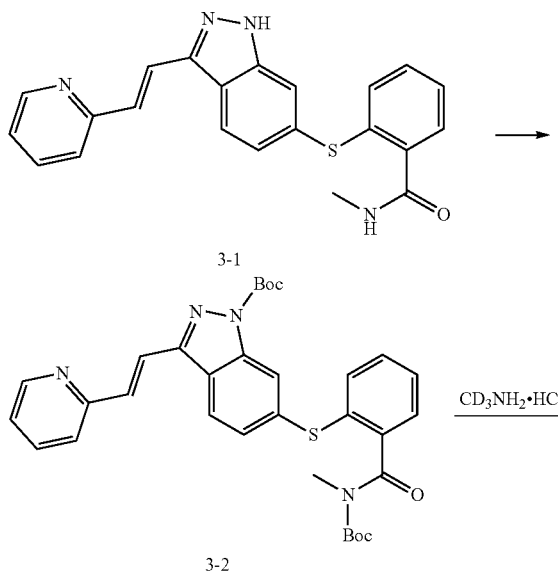

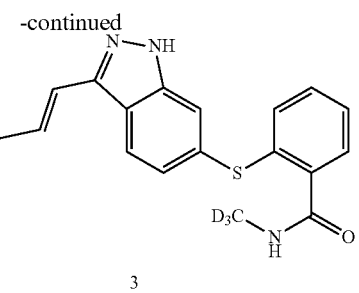

(1) Axitinib (3-1, 193 mg, 0.5 mmol, 1.0 eq) was dissolved in $CH_2Cl_2$ (10 mL), to which was added DMAP (183 mg, 1.5 mmol) under stirring, followed by addition of Boc anhydride (327 mg, 1.5 mmol). The resultant mixture was allowed to react 16 h at room temperature, till the reaction was completed by TLC detection. The reaction system was washed with 0.1 N HCl aqueous solution until DMAP was cleaned off. The organic layer was washed with saturated NaHCO$_3$ aqueous solution and NaCl aqueous solution, respectively, then dried with anhydrous Na$_2$SO$_4$, rotatory evaporated, and purified by thin-layer column chromatography (PE/EA=2:1), to obtain white solid product 6-((2-((t-butoxycarbonyl)(methyl)carbamoyl)phenyl)thio)-3-(2-(pyridin-2-yl)ethylenyl-1H-indazol-1-carboxylic acid (E)-t-butyl ester (3-2), with a yield of 81.9%.

$^1$H NMR (400 MHz, CDCl3) δ 8.65 (d, J=4.0 Hz, 1H), 8.02 (s, 1H), 7.93 (t, J=10.6 Hz, 2H), 7.77 (d, J=15.6 Hz, 2H), 7.51 (d, J=6.5 Hz, 1H), 7.46-7.41 (m, 1H), 7.39-7.32 (m, 3H), 7.28 (dd, J=8.5, 1.5 Hz, 2H), 3.26 (s, 3H), 1.62 (s, 9H), 1.22 (s, 9H).

(2) Previous product 6-((2-((t-butoxycarbonyl)(methyl) carbamoyl)phenyl)thio)-3-(2-(pyridin-2-yl) ethylenyl-1H-indazol-1-carboxylic acid (E)-t-butyl ester (3-2, 117.2 mg, 0.2 mmol) was dissolved in 5 mL acetonitrile, to which was added deuterated methylamine hydrochloride (56 mg, 0.8 mmol), followed by addition of DBU (136 mg, 0.92 mmol). The resultant mixture reacted overnight at room temperature. The reaction was completed by TLC detection. The resultant mixture was washed with water and extracted with ethyl acetate. The organic layer was successively washed with 0.1 N HCl aqueous solution, saturated NaHCO$_3$ aqueous solution and NaCl aqueous solution, respectively, and then dried with anhydrous Na$_2$SO$_4$, rotatory evaporated, to obtain yellowish solid product (E)-N-(deuterated methyl)-2-(3-(2-(2-pyridinyl)ethylenyl)-1H-indazol-6-yl)thioamide) (3, 75 mg), with a yield of 96.4%.

MS (ESI) m/z 390 (M+H)$^+$.

$^1$H NMR (400 MHz, DMSO-d$_6$) δ 13.36 (s, 1H), 8.61 (d, J=3.8 Hz, 1H), 8.42-8.35 (m, 1H), 8.22 (d, J=8.5 Hz, 1H), 7.95 (d, J=16.4 Hz, 1H), 7.81 (td, J=7.7, 1.8 Hz, 1H), 7.67 (d, J=7.8 Hz, 1H), 7.63-7.54 (m, 2H), 7.49 (dd, J=7.3, 1.7 Hz, 1H), 7.33-7.25 (m, 3H), 7.19 (dd, J=8.5, 1.1 Hz, 1H), 7.03 (dd, J=7.7, 1.1 Hz, 1H).

Example 4 Synthesis of Compound 4

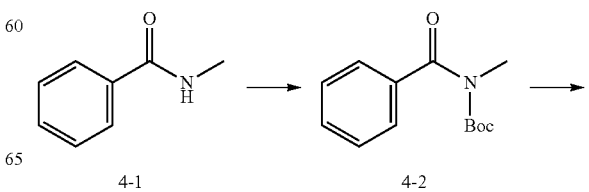

-continued

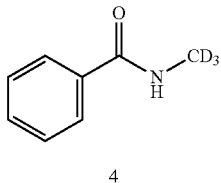

4

(1) N-methylbenzamide (4-1, 135 mg, 1 mmol) was dissolved in CH$_2$Cl$_2$ (5 mL), to which was added DMAP (244 mg, 2 mmol) under stirring, followed by addition of Boc anhydride (436 mg, 2 mmol). The resultant mixture was allowed to react 16 h at room temperature, till the reaction was completed by TLC detection. The reaction system was washed with 0.1 N HCl aqueous solution until DMAP was cleaned off. The organic layer was washed with saturated NaHCO$_3$ aqueous solution and NaCl aqueous solution, respectively, then dried with anhydrous Na$_2$SO$_4$, rotatory evaporated, and purified by thin-layer column chromatography (PE/EA=2:1), to obtain white solid product (4-2, 220 mg), with a yield of 93.6%.

MS (ESI) m/z 180.1 [M−56+H]$^+$.

(2) Previous product (4-2, 118 mg, 0.5 mmol) was dissolved in 2 mL acetonitrile, to which was added deuterated methylamine hydrochloride (105 mg, 1.5 mmol), followed by addition of DBU (304 mg, 2 mmol). The resultant mixture reacted overnight at 25° C. under stirring and then cooled to room temperature. The reaction was completed by TLC detection. The resultant mixture was washed with water and extracted with ethyl acetate. The organic layer was successively washed with 0.1 N HCl aqueous solution, saturated NaHCO$_3$ aqueous solution and NaCl aqueous solution, respectively, and then dried with anhydrous Na$_2$SO$_4$, rotatory evaporated, to obtain white solid product (4, 57 mg), with a yield of 82.6%.

MS (ESI) m/z 139.1 [M+H]$^+$.

$^1$H NMR (400 MHz, CDCl$_3$) δ 7.76 (m, 2H), 7.47 (dd, J=8.5, 6.1 Hz, 1H), 7.40 (t, J=7.4 Hz, 2H), 6.37 (s, 1H).

Example 5 Synthesis of Compound 5

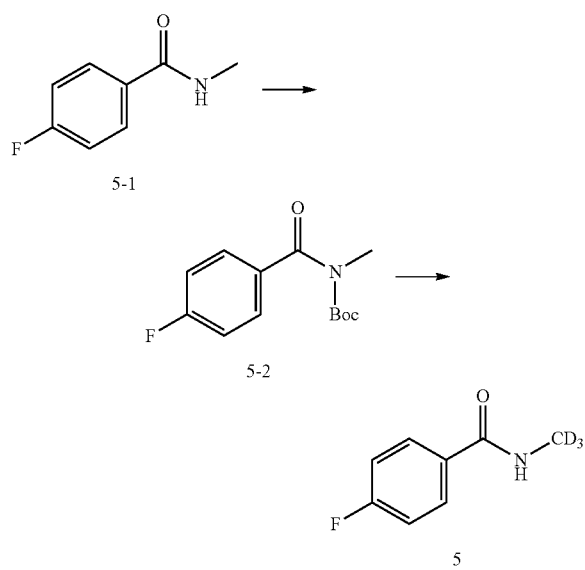

(1) 5-1 (153 mg, 1 mmol) was dissolved in CH$_2$Cl$_2$ (5 mL), to which was added DMAP (244 mg, 2 mmol) under stirring, followed by addition of Boc anhydride (436 mg, 2 mmol). The resultant mixture was allowed to react 16 h at room temperature, till the reaction was completed by TLC detection. The reaction system was washed with 0.1 N HCl aqueous solution until DMAP was cleaned off. The organic layer was washed with saturated NaHCO$_3$ aqueous solution and NaCl aqueous solution, respectively, then dried with anhydrous Na$_2$SO$_4$, rotatory evaporated, and purified by thin-layer column chromatography (PE/EA=2:1), to obtain white solid product (5-2, 200 mg), with a yield of 93.6%.

MS (ESI) m/z 198.2 ([M−56+H]$^+$).

(2) Previous product (5-2, 118 mg, 0.5 mmol) was dissolved in 2 mL acetonitrile, to which was added deuterated methylamine hydrochloride (105 mg, 1.5 mmol), followed by addition of DBU (304 mg, 2 mmol). The resultant mixture reacted overnight at 25° C. under stirring and then cooled to room temperature. The reaction was completed by TLC detection. The resultant mixture was washed with water and extracted with ethyl acetate. The organic layer was successively washed with 0.1 N HCl aqueous solution, saturated NaHCO$_3$ aqueous solution and NaCl aqueous solution, respectively, and then dried with anhydrous Na$_2$SO$_4$, rotatory evaporated, to obtain white solid product (5, 57 mg), with a yield of 82.6%.

MS (ESI) m/z 157.3 ([M+H]$^+$).

$^1$H NMR (400 MHz, CDCl$_3$) δ 7.77 (dd, J=8.7, 5.3 Hz, 2H), 7.11 (t, J=8.6 Hz, 2H), 6.12 (s, 1H).

Example 6 Synthesis of Compound 6

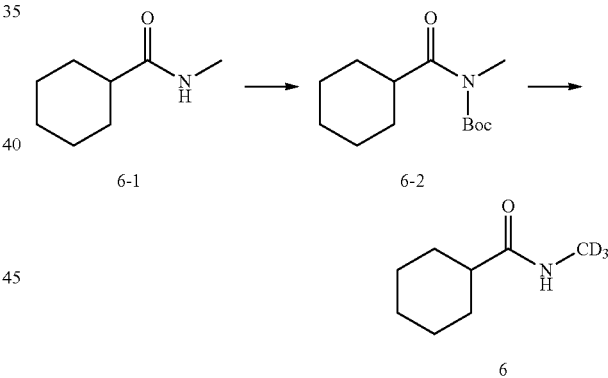

(1) N-methylcyclohexanecarboxamide (6-1, 141 mg, 1 mmol) was dissolved in CH$_2$Cl$_2$ (5 mL), to which was added DMAP (244 mg, 2 mmol) under stirring, followed by addition of Boc anhydride (436 mg, 2 mmol). The resultant mixture was allowed to react 16 h at room temperature, till the reaction was completed by TLC detection. The reaction system was washed with 0.1 N HCl aqueous solution until DMAP was cleaned off. The organic layer was washed with saturated NaHCO$_3$ aqueous solution and NaCl aqueous solution, respectively, then dried with anhydrous Na$_2$SO$_4$, rotatory evaporated, and purified by thin-layer column chromatography (PE/EA=2:1), to obtain white solid product (6-2, 220 mg), with a yield of 83.8%.

MS (ESI) m/z 186.1 ([M−56+H]$^+$).

(2) Previous product (6-2, 120 mg, 0.5 mmol) was dissolved in 2 mL acetonitrile, to which was added deuterated methylamine hydrochloride (105 mg, 1.5 mmol), followed by addition of DBU (304 mg, 2 mmol). The resultant mixture reacted overnight at room temperature. The reaction was completed by TLC detection. The resultant mixture was washed with water and extracted with ethyl acetate. The organic layer was successively washed with 0.1 N HCl aqueous solution, saturated NaHCO$_3$ aqueous solution and NaCl aqueous solution, respectively, and then dried with anhydrous Na$_2$SO$_4$, rotatory evaporated, to obtain white solid product (6, 62 mg), with a yield of 86.1%.

MS (ESI) m/z 145.1 ([M+H]$^+$).

$^1$H NMR (400 MHz, CDCl$_3$) δ 5.6 (s, 1H), 2.05 (tt, J=9.2, 5.9 Hz, 1H), 1.75 (m, 4H), 1.41 (m, 2H), 1.25 (m, 4H).

Example 7 Synthesis of Compound 7

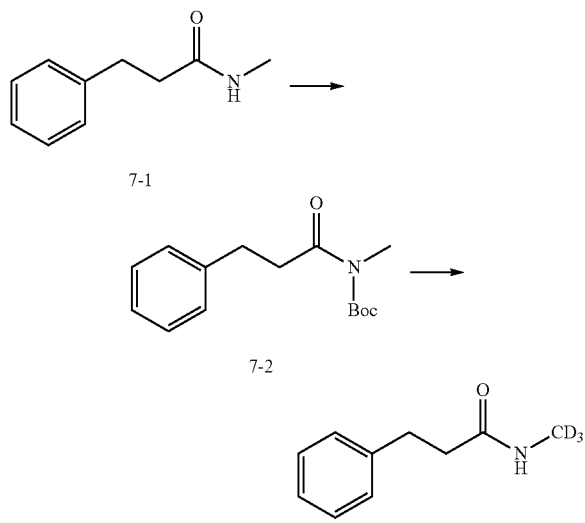

(1) N-methyl-3-phenylpropionamide (7-1, 163 mg, 1 mmol) was dissolved in CH$_2$Cl$_2$ (5 mL), to which was added DMAP (244 mg, 2 mmol) under stirring, followed by addition of Boc anhydride (436 mg, 2 mmol). The resultant mixture was allowed to react 16 h at room temperature, till the reaction was completed by TLC detection. The reaction system was washed with 0.1 N HCl aqueous solution until DMAP was cleaned off. The organic layer was washed with saturated NaHCO$_3$ aqueous solution and NaCl aqueous solution, respectively, then dried with anhydrous Na$_2$SO$_4$, rotatory evaporated, and purified by thin-layer column chromatography (PE/EA=2:1), to obtain white solid product (7-2, 214 mg), with a yield of 81.4%.

MS (ESI) m/z 208.1 ([M−56+H]$^+$).

(2) Previous product (7-2, 131 mg, 0.5 mmol) was dissolved in 2 mL acetonitrile, to which was added deuterated methylamine hydrochloride (105 mg, 1.5 mmol), followed by addition of DBU (304 mg, 2 mmol). The resultant mixture reacted overnight at room temperature. The reaction was completed by TLC detection. The resultant mixture was washed with water and extracted with ethyl acetate. The organic layer was successively washed with 0.1 N HCl aqueous solution, saturated NaHCO$_3$ aqueous solution and NaCl aqueous solution, respectively, and then dried with anhydrous Na$_2$SO$_4$, rotatory evaporated, to obtain white solid product (7, 73 mg), with a yield of 88.1%.

MS (ESI) m/z 167.1 ([M+H]$^+$).

$^1$H NMR (400 MHz, CDCl$_3$) δ 7.3 (m, 2H), 7.19 (t, J=6.2 Hz, 3H), 5.57 (s, 1H), 2.96 (t, J=7.8 Hz, 2H), 2.46 (t, J=7.8 Hz, 2H).

Example 8 Synthesis of Compound 8

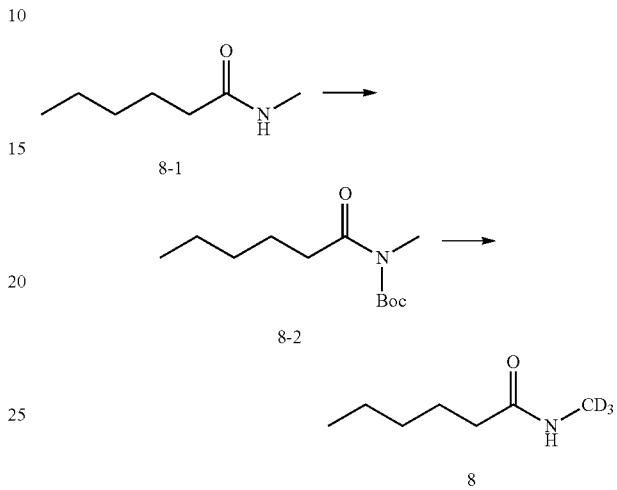

(1) N-methylhexanamide (8-1, 129 mg, 1 mmol) was dissolved in CH$_2$Cl$_2$ (5 mL), to which was added DMAP (244 mg, 2 mmol) under stirring, followed by addition of Boc anhydride (436 mg, 2 mmol). The resultant mixture was allowed to react 16 h at room temperature, till the reaction was completed by TLC detection. The reaction system was washed with 0.1 N HCl aqueous solution until DMAP was cleaned off. The organic layer was washed with saturated NaHCO$_3$ aqueous solution and NaCl aqueous solution, respectively, then dried with anhydrous Na$_2$SO$_4$, rotatory evaporated, and purified by thin-layer column chromatography (PE/EA=2:1), to obtain white solid product (8-2, 199 mg), with a yield of 86.9%.

MS (ESI) m/z 174.1 ([M−56+H]$^+$).

(2) Previous product (8-2, 115 mg, 0.5 mmol) was dissolved in 2 mL acetonitrile, to which was added deuterated methylamine hydrochloride (105 mg, 1.5 mmol), followed by addition of DBU (304 mg, 2 mmol). The resultant mixture reacted overnight at room temperature. The reaction was completed by TLC detection. The resultant mixture was washed with water and extracted with ethyl acetate. The organic layer was successively washed with 0.1 N HCl aqueous solution, saturated NaHCO$_3$ aqueous solution and NaCl aqueous solution, respectively, and then dried with anhydrous Na$_2$SO$_4$, rotatory evaporated, to obtain white solid product (8, 56 mg), with a yield of 84.8%.

$^1$H NMR (400 MHz, CDCl$_3$) δ 6.16 (s, 1H), 2.12 (t, J=7.7 Hz, 2H), 1.58 (m, 2H), 1.23 (dd, J=8.6, 4.9 Hz, 4H), 0.82 (t, J=6.8 Hz, 3H).

MS (ESI) m/z 133.1 ([M+H]$^+$).

In summary, the present invention provides a new method for synthesis of deuterated amides and deuterated sulfonamides, in which the reaction conditions are mild, and the route is short, including only two steps. The method can be applied to raw materials unsuitable for using prior art, improve the synthetic efficiency, and used for many amide compounds, with an incredible versatility, thereby providing a new choice for preparation of deuterated amide and sulfonamide compounds.

The invention claimed is:

1. A method for synthesizing deuterated amine, comprising the steps of a first step of adding compound M, DMAP, and R³—X to a first solvent for reaction to obtain compound N; and a second step of adding compound N, R⁴—NH—R⁵ or a salt thereof, and a base to a second solvent for reaction to obtain a deuterated amine compound I,

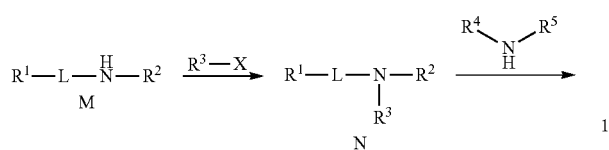

wherein:
L is carbonyl or sulfonyl;
R¹ is

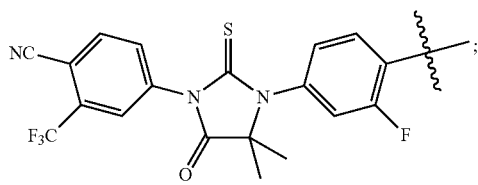 [SMILES: *c1ccc(N2C(=S)N(c3ccc(C#N)c(C(F)(F)F)c3)C(=O)C2(C)C)cc1F]

R² is selected from the group consisting of substituted or unsubstituted alkyl, substituted or unsubstituted cycloalkyl, substituted or unsubstituted heterocyclic group, substituted or unsubstituted aryl, and substituted or unsubstituted heteroaryl;
R³ is —CO—R⁶ or —SO2R⁷ and X is a leaving group, wherein, R⁶ and R⁷ are independently selected from alkoxy, alkyl, substituted alkyl, and aryl;
R⁴ and R⁵ are independently selected from H, substituted or unsubstituted deuterated alkyl, deuterated cycloalkyl, deuterated heterocyclic group, deuterated aryl, and deuterated heteroaryl, with the proviso that R⁴ and R⁵ are not hydrogen at the same time;
wherein, in the first step, a yield for the compound N thus synthesized is 92.3%, and
wherein, in the second step, a yield for the deuterated amine compound I thus synthesized is 92.8%.

2. The synthetic method according to claim 1, wherein R³ is selected from —CO—R⁶ or —SO2R⁷, X is selected from —OR³, Cl, and Br, wherein R⁶ and R⁷ are independently selected from t-butoxy, isopropoxy, benzyloxy, methyl, trifluoromethyl, phenyl, and tolyl.

3. The synthetic method according to claim 2, wherein R⁶ is selected from t-butoxy, isopropoxy, and benzyloxy, and R⁷ is selected from methyl, trifluoromethyl, phenyl, and tolyl.

4. The synthetic method according to claim 3, wherein R³ is —CO—R⁶, X is —OR³, and R⁶ is t-butoxy.

5. The synthetic method according to claim 1, wherein R⁴ and R⁵ are independently selected from H and deuterated alkyl, with the proviso that R⁴ and R⁵ are not hydrogen at the same time.

6. The synthetic method according to claim 5, wherein R⁴ and R⁵ are independently selected from H and deuterated methyl, with the proviso that R⁴ and R⁵ are not hydrogen at the same time.

7. The synthetic method according to claim 1, wherein R² is a substituted or unsubstituted C1-C6 alkyl.

8. The synthetic method according to claim 7, wherein R² is a substituted or unsubstituted C1-C4 alkyl.

9. The synthetic method according to claim 8, wherein R² is methyl.

10. The synthetic method according to claim 1, wherein compound I is

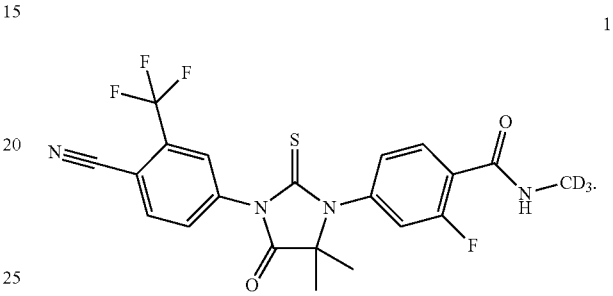

11. The synthetic method according to claim 1, wherein in the first step, the first solvent is a polar solvent selected from the group consisting of dichloromethane, dichloroethane, formamide, trifluoroacetic acid, DMSO, acetonitrile, DMF, hexamethylphosphoramide, methanol, ethanol, acetic acid, isopropanol, pyridine, tetramethylethylenediamine, acetone, triethylamine, n-butanol, dioxane, tetrahydrofuran, methyl formate, tributylamine, methyl ethyl ketone, ethyl acetate, chloroform, trioctylamine, dimethyl carbonate, ethyl ether, isopropyl ether, n-butyl ether, trichloroethylene, and diphenyl ether.

12. The synthetic method according to claim 1, wherein in the first step, the first solvent is a non polar solvent selected from the group consisting of benzene, toluene, carbon tetrachloride, carbon disulfide, cyclohexane, and hexane.

13. The synthetic method according to claim 1, wherein, in the first step, a molar ratio of compound M, DMAP, and R³—X is 1:1-3:1-10.

14. The synthetic method according to claim 1, wherein, in the first step, a ratio of compound M and the first solvent is 1:2-20 mmol/mL.

15. The synthetic method according to claim 1, wherein a reaction temperature of the first step is 10-60° C.

16. The synthetic method according to claim 1, wherein a reaction time of the first step is 10-120 h.

17. The synthetic method according to claim 1, wherein, in the second step, the second solvent is a polar solvent or a non-polar solvent.

18. The synthetic method according to claim 17, wherein said polar solvent is selected from the group consisting of dichloromethane, dichloroethane, formamide, trifluoroacetic acid, DMSO, acetonitrile, DMF, hexamethylphosphoramide, methanol, ethanol, acetic acid, isopropanol, pyridine, tetramethylethylenediamine, acetone, triethylamine, n-butanol, dioxane, tetrahydrofuran, methyl formate, tributylamine, methyl ethyl ketone, ethyl acetate, chloroform, trioctylamine, dimethyl carbonate, ethyl ether, isopropyl ether, n-butyl ether, trichloroethylene, and diphenyl ether.

19. The synthetic method according to claim 17, wherein said non polar solvent is selected from the group consisting of benzene, toluene, carbon tetrachloride, carbon disulfide, cyclohexane, and hexane.

20. The synthetic method according to claim 1, wherein, in the second step, a ratio of compound N and the second solvent is 1:1-25 mmol/mL.

21. The synthetic method according to claim 1, wherein, in the second step, said base is an organic base selected from the group consisting of DBU, sodium methoxide, potassium ethoxide, potassium t-butoxide, sodium t-butoxide, triethylamine, triethylenediamine, DBN, DMAP, pyridine, N-methylmorpholine, tetramethylethylenediamine, TMG, n-butyl lithium, and LDA.

22. The synthetic method according to claim 1, wherein, in the second step, said base is an inorganic base selected from the group consisting of potassium hydroxide, barium hydroxide, calcium hydroxide, aluminum hydroxide, lithium hydroxide, magnesium hydroxide, zinc hydroxide, copper hydroxide, iron hydroxide, lead hydroxide, cobalt hydroxide, chromium hydroxide, zirconium hydroxide, nickel hydroxide, ammonium hydroxide, sodium carbonate, sodium bicarbonate, potassium carbonate, and potassium bicarbonate.

23. The synthetic method according to claim 1, wherein, in the second step, a molar ratio of compound N, $R^4$—NH—$R^5$ or its salt, and base is 1:1-4:1-5.

24. The synthetic method according to claim 23, wherein the molar ratio of compound N, $R^4$—NH—$R^5$ or its salt, and base is 1:3:4.

25. The synthetic method according to claim 1, wherein a reaction temperature of the second step is 10-100° C.

26. The synthetic method according to claim 1, wherein a reaction time of the second step is 10-120 h.

* * * * *